United States Patent [19]

Uwajima et al.

[11] Patent Number: 4,677,062

[45] Date of Patent: Jun. 30, 1987

[54] PROCESS FOR PRODUCING BILIRUBIN OXIDASE

[75] Inventors: Takayuki Uwajima, Machida; Mayumi Ando, Yokohama, both of Japan

[73] Assignee: Kyowa Hakko Kogyo Co., Ltd., Tokyo, Japan

[21] Appl. No.: 885,391

[22] PCT Filed: Apr. 27, 1984

[86] PCT No.: PCT/JP84/00223

§ 371 Date: Dec. 26, 1984

§ 102(e) Date: Dec. 26, 1984

[87] PCT Pub. No.: WO84/04328

PCT Pub. Date: Nov. 8, 1984

Related U.S. Application Data

[62] Division of Ser. No. 694,450, Dec. 26, 1984, abandoned.

[30] Foreign Application Priority Data

Apr. 28, 1983 [JP] Japan .................. 58-75587

[51] Int. Cl.$^4$ .................................. C12P 21/00
[52] U.S. Cl. .................................. 435/68; 435/189; 435/911; 435/254
[58] Field of Search .................. 435/189, 68, 25, 254, 435/911

[56] References Cited

U.S. PATENT DOCUMENTS 4,211,844  7/1980  Wu ........................ 435/189
4,554,249  11/1985  Kosaka .................. 435/269

FOREIGN PATENT DOCUMENTS 0033462  8/1981  European Pat. Off. ......... 435/25
2521583  8/1983  France .................. 1/26
0159487  10/1982  Japan .................. 435/189
2134116  8/1984  United Kingdom .................. 9/02

OTHER PUBLICATIONS

Murao et al, (1981), Chemical Abstracts, 1982, vol. 96, No. 2, p. 229, Item #64651c.
Roesch et al, (1970), Chemical Abstracts, 1970, vol. 73, No. 25, p. 125, Item #128157f.
Gavrilova et al, (1983), Chemical Abstracts, vol. 99, No. 5, p. 319, Item #36017u.
Fedorov, (1970), Chemical Abstracts, 1971, vol. 74, No. 21, p. 109, Item #10846g.
Jackuliak, (1978), Chemical Abstracts, 1979, vol. 90, No. 9, p. 240, Item #68908r.
Tsuruta, (1983), Chemical Abstracts, (1983), vol. 99, No. 17, p. 343, Item #136825z.
Cheung et al, Chemical Abstracts, 1969, vol. 70, No. 23, p. 25, Item #103134w.
Watanabe et al, (1982), Chemical Abstracts, vol. 97, No. 9, p. 269, Item #68424z.

*Primary Examiner*—Sam Rosen
*Assistant Examiner*—William J. Herald
*Attorney, Agent, or Firm*—Fitzpatrick, Cella, Harper & Scinto

[57] ABSTRACT

Novel bilirubin oxidase inactive against phenol, catechol, and hydroquinone, and a process for preparing said enzyme by recovering it from a culture liquor of bilirubin oxidase producing microorganisms belonging to the genus Coprinus, Trametes, Coriolus, Pholiota, Pleurotus, Lenzites, or Fomitopsis. This enzyme can decompose bilirubin when added to a bilirubin-containing solution, and makes it possible to assay bilirubin by measuring a decrease in absorption in the visible region of the reaction solution. Thus, it can be used for assaying bilirubin and for removing it from a sample to avoid its interference in determining a substrate or an enzyme activity.

2 Claims, 3 Drawing Figures

1

PROCESS FOR PRODUCING BILIRUBIN OXIDASE

This application is a division of application Ser. No. 694,450 filed Dec. 26, 1984, now abandoned.

Technical Field

The present invention relates to a novel bilirubin oxidase showing strong specific activities on bilirubin and biliverdin, a process for the production thereof using Basidiomvcetes and a method of quantitative determination for diagnostic purposes utilizing the enzyme.

BACKGROUND ART

Heretofore, a bilirubin oxidase produced by culturing a microorganism belonging to the genus Aqaricus is known, whose properties have not been clarified (Japanese Published Unexamined Patent Application No. 151193/79). Also, it is reported that a bilirubin oxidase is produced by culturing a microorganism belonging to the genus Myrothecium [N. Tanaka and S. Murao, Agric. Biol. Chem., 46, 2499–2503 (1982)]. This known enzyme shows specific activities on hydroquinone and catechol in addition to bilirubin and biliverdin. As a result of various studies of bilirubin oxidase, it has been found that a wide range of microorganisms of Basidiomycetes produce a novel bilirubin oxidase.

DISCLOSURE OF THE INVENTION

In further detail, the properties of the novel enzyme of the present invention are given.

The following method is adopted for the determination of the enzyme activity.

To 0.5 ml of a solution containing 0.01% bilirubin, 0.5 ml of 0.1M TES buffer solution (pH 7.0), 1.9 ml of $H_2O$ and 0.1 ml of a solution of the bilirubin oxidase according to the present invention are added. The mixture is incubated at 37° C. for 5 minutes with shaking and a decrease in absorption at 440 nm of bilirubin in the reaction solution is measured to determine the enzyme activity. One unit of enzyme activity is defined as the amount of the enzyme that oxidizes one μmole of bilirubin per minute at a temperature of 37° C. using 56.3 of the molecular extinction coefficient of bilirubin.

Furthermore, the amount of enzyme protein is determined according to Lowry's method [O. H. Lowry, N.J. Rosebrough, A. L. Fav and R. J. Randall, J. Biol. Chem., 193, 265 (1951)] using a Copper-Falin's reagent.

1. Action

The enzyme catalyzes the oxidation of bilirubin into water, not hydrogen peroxide in the presence of oxygen molecularity. FIG. 1 illustrates decrease with the elapse of time in the absorption of bilirubin in the visible region when bilirubin is decomposed with the enzyme. Also, the enzyme catalyzes the oxidation of biliverdin, and the rate at which the oxidation proceeds in slower than that of bilirubin. FIG. 2 illustrates the amounts of oxygen consumed in the initial stage of reactions in which bilirubin and biliverdin are used as the substrate.

2. Optimum pH
6–9

3. Stable pH range
Stable at a pH of 5–11 in an incubation at 37° C. for 60 minutes.

4. Optimum temperature
50°–60° C.

5. Temperature stability
The enzyme keeps 90–95% of its activity in an incubation in 0.1M TES buffer solution (pH 8.0) at 60° C. for 15 minutes.

6. Molecular weight
The molecular weight of the enzyme is calculated to be about 44,000 by the gel-filtration method in Sephadex G-100.

7. Isoelectric point
The isoelectric point of the enzyme is 3.98 as determined by the electrophoretic focussing method.

8. Absorption spectrum
The purified preparation of the enzyme exhibits its absorption maxima at 280 nm and 600 nm, and is a copper protein (FIG. 3).

According to the present invention, this novel bilirubin oxidase is obtained by culturing a microorganism belonging to the genus Coprinus, Trametes, Coriolus, Pholiota, Pleurotus, Lenzites or Fomitopsis and which is capable of producing the bilirubin oxidase, in a medium until the enzyme is formed and accumulated in the culture liquor and thereafter recovering the bilirubin oxidase therefrom.

Any microorganism may be used in the present invention so long as it belongs to the genus Coprinus, Trametes, Coriolus, Pholiota, Pleurotus, Lenzites or Fomitopsis and is capable of producing bilirubin oxidase.

Examples of the preferred strain include *Coprinus micaceus* HU8302 (NRRL 15400), *Trametes hirsuta* HU8311 (NRRL 15401), *Trametes versicolor* HU8312 (NRRL 15402), *Coriolus consors* HU8313 (NRRL 15403), *Pholiota nameko* HU8321 (NRRL 15404), *Pleurotus ostreatus* HU8331 (NRRL 15405), *Lenzites styracina* HU8341 (NRRL 15406) and *Fomitopsis castanea* HU8351 (NRRL 15407). The mycological properties of the strains are described in Genshoku Nihon Kinrui Zukan (Primary Color Japanese Microorganism Pictorial Book) by Rokuya Imazeki and Tsugio Hongo, printed by Hoikusha (1965). These strains were deposited under Budapest Treaty with the Agricultural Research Culture Collection (NRRL) in Illinois, U.S.A. on Apr. 18, 1983 under the above deposit numbers.

As the medium to be used in the present invention, either a synthetic or natural medium may be used as long as it properly contains a carbon source, a nitrogen source, minerals and other nutrients. As the carbon source, sugars such as glucose, sucrose and blackstrap molasses, sugar alcohols such as glycerol, sorbitol and mannitol, and the like are used. As the nitrogen source, there may be employed ammonia, various inorganic and organic ammonium salts such as ammonium chloride, ammonium sulfate, ammonium carbonate, ammonium acetate and ammonium phosphate, nitrogenous compounds such as urea, and mitrogen-containing organic materials such as peptone, yeast extract, casein hydrolyzate, defatted soybean and its digested product. As the inorganic materials, salts of metals such as sodium, potassium, manganese, magnesium, calcium and copper, and salts of inorganic acids such as phospholic acid, sulfuric acid, nitric acid and hydrochloric acid are appropriate.

Generally, culturing is carried out at a temperature of 20°–40° C., preferably 25°–30° C. At the beginning of the culturing, the pH is maintained at 5.5–7.5, preferably around 6. Under these conditions, culturing is carried out with shaking or submerged agitation for 4–6 days. Thus, a considerable amount of bilirubin oxidase is formed in the culture broth.

After completion of the culturing, to recover the enzyme from the resulting culture broth, conventional means of recovering enzymes are used. The enzyme is mostly accumulated in the culture filtrate rather than within the microbial cells. Generally, the microbial cells are removed from the culture broth to obtain a crude enzyme solution. Extraction of bilirubin oxidase is, for example, carried out in the following manner. To the crude enzyme solution is added ammonium sulfate to 80% saturation, and the mixture is allowed to stand at 4° C. overnight. A filter aid is added to collect precipitated fractions. The precipitates are dialyzed against 0.01M phosphate buffer solution (pH 7.0) thoroughly and centrifuged to obtain a supernatant. The supernatant is subjected to conventional treatments for enzyme purification such as iron exchange column chromatography using DEAE-cellulose, QAE-Sephadex, etc., gel-filtration using Sephadex G-200, Sephalose 6B, etc. and adsorption extraction using hydroxyapatite, in combination. Thus, purified bilirubin oxidase is recovered.

Using bilirubin oxidase according to the present invention, the quantitative determination of bilirubin can be carried out.

In the determination, a bilirubin-containing sample is subjected to an enzyme reaction to decompose bilirubin. The decreased amount of bilirubin in the reaction mixture is determined by measuring the absorption of the reaction mixture at 440 nm.

Generally, bilirubin oxidase is dissolved in a suitable buffer such as phosphate buffer to prepare a 0.01-2 unit/ml enzyme solution, and the enzyme solution is added to a sample. The mixture is incubated at 15°-45° C. for 5-60 minutes, and the calibration curve is prepared using a bilirubin standard solution to determine the amount of bilirubin in a sample.

Furthermore, the present enzyme can be used for removing bilirubin from a sample to avoid interference of bilirubin in determining a substrate or an enzyme activity.

Namely, various methods for the determination of a substrate which comprises adding an enzyme to a sample to decompose a substrate, carrying out an enzyme reaction and determining the formed product are known. Specifically, in the case where an enzyme is an oxidase and one of the products is hydrogen peroxide, though determination methods are simple, the existence of bilirubin in a sample is likely to have an influence on a result. However, bilirubin contained in a sample have been decomposed by adding the present enzyme; and thereafter the oxidase is added and the formed hydrogen peroxide is determined to thereby obtain more accurate results.

Hydrogen peroxide is, in general, determined by reacting hydrogen peroxide with a chromogen to form a pigment, and measuring the absorption of the colored reaction solution. As the chromogen used therein, phenols such as 4-aminoantipyrine and phenol are frequently used.

In the case where an object of measurement is the enzyme activity, the same method as described above is adopted except that a substrate is added to a sample to thereby obtain more accurate results.

As the substrate to be determined, cholesterol, neutral fat, uric acid, etc. are exemplified.

In the determination of these substrates, bilirubin in a sample is decomposed by the foregoing method, and thereafter a conventional method is adopted to attain the purpose. That is, the purpose is attained by adding a reagent solution containing a reagent, a substrate, a chromogen, a surfactant, etc. necessary to determine a substrate or enzyme activity, carrying out a reaction and measuring the absorption of the reaction solution at absorption maximum wavelength of the chromogen.

BEST MODE FOR CARRYING OUT THE INVENTION

Figure 1:
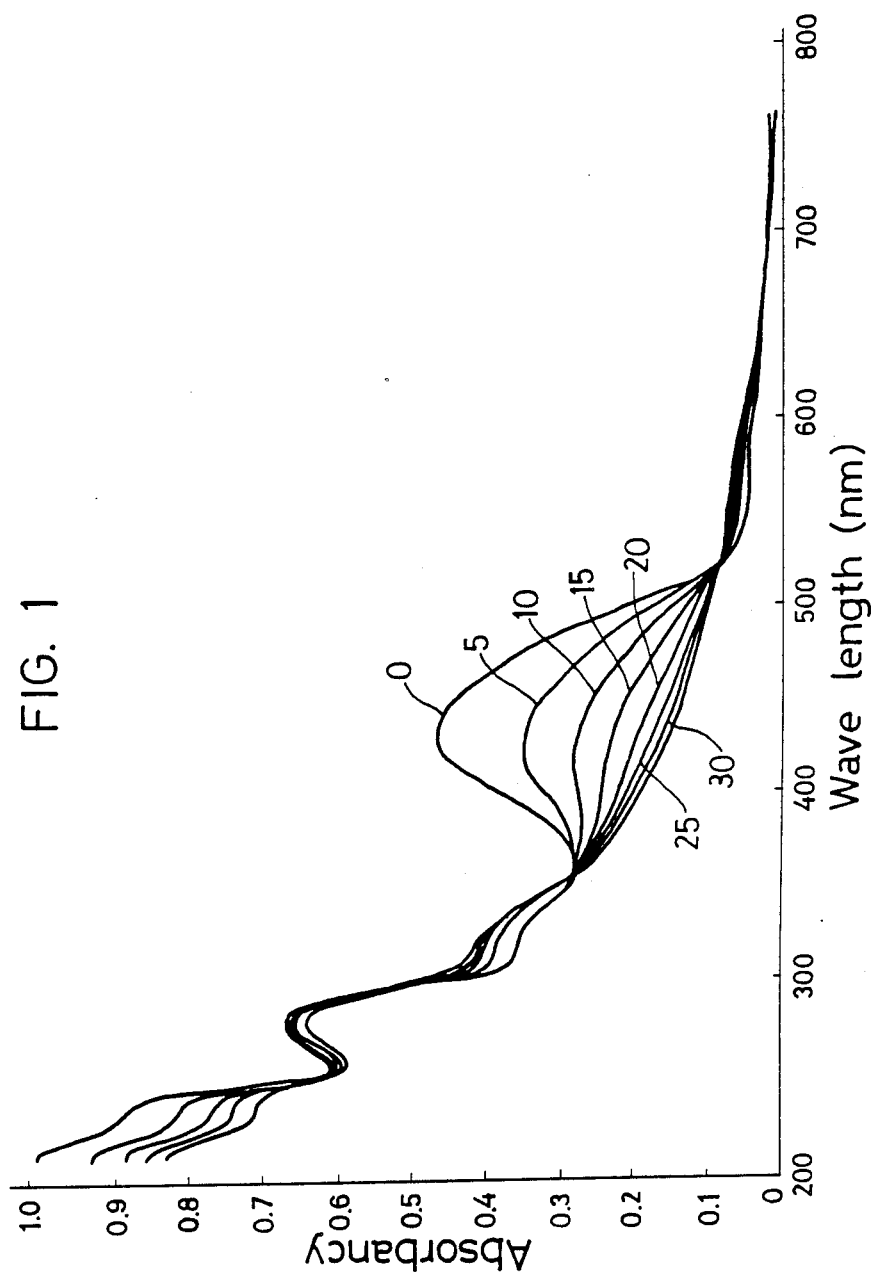
FIG. 1 illustrates decrease with the elapse of time in the absorption of bilirubin in the visible region when bilirubin undergoes the activity of the present enzyme.
Figure 2:
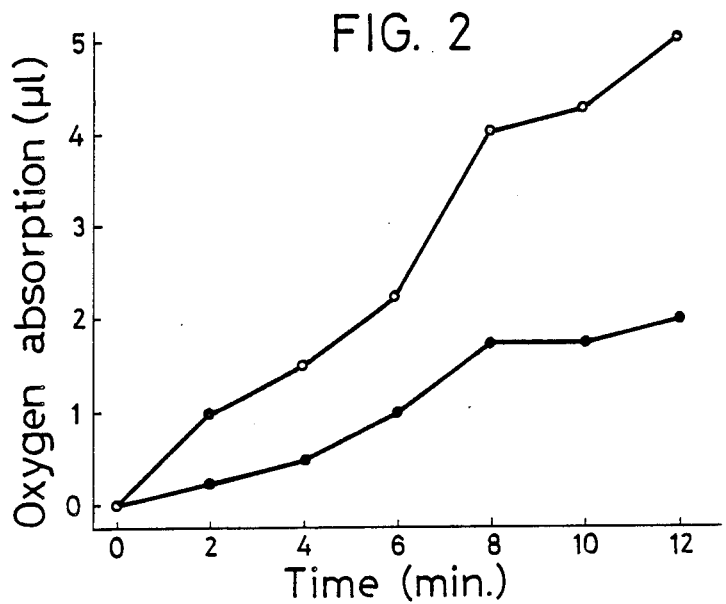
FIG. 2 illustrates the amounts of oxygen absorption in the cases of bilirubin and biliverdin as the substrate.
1: bilirubin
2: biliverdin
Figure 3:
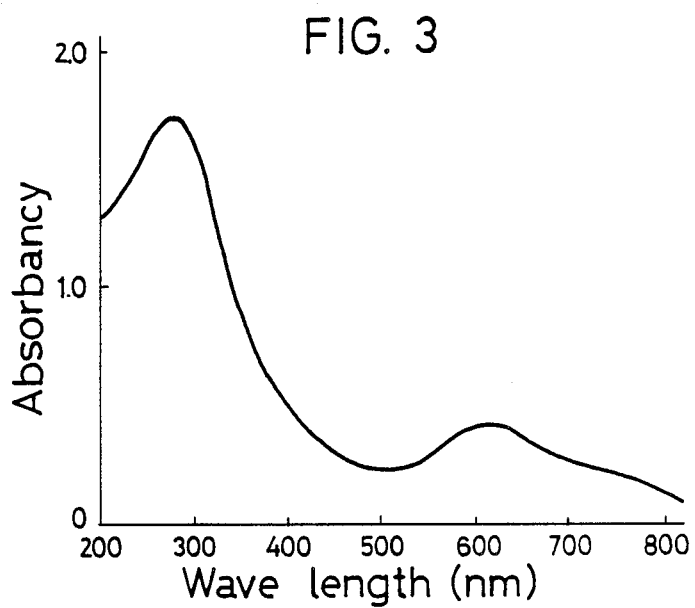
FIG. 3 illustrates absorption spectrum of the present enzyme.

Certain specific embodiments of the present invention are illustrated by the following examples.

EXAMPLE 1

*Coprinus micaceus* HU8302 is inoculated into 0.3 l of a culture medium (pH 6.5) comprising 3% glucose, 2% sucrose, 1.5% protein powder, 0.5% CSL (corn steep liquor), 0.1% $K_2HPO_4$, 0.05% $MgSO_4.7H_2O$, 10 mg/l $FeCl_3.6H_2O$ and 2 mg/l vitamin $B_2$ in each of three 2 l-Erlenmeyer flasks provided with baffles, and cultured with shaking at 28° C. for 4 days. Then, a resulting seed culture is inoculated into a 30 l-jar containing 15 l of a sterilized culture medium of the same composition as mentioned above, and cultured with aeration-stirring at an aeration rate of 15 l/min., a stirring speed of 250 rpm at 28° C. for 4 days. After the completion of the culturing, the microbial cells are filtered off using a Buchner funnel to obtain a 10.5 l of a culture filtrate (4.08 unit/ml). To the filtrate (crude enzyme solution) is added ammonium sulfate of 0-80% saturation, and the precipitated fractions are dissolved in 0.01M phosphate buffer (pH 7.0). The solution is dialyzed using dialysis membrane of cellulose tube against the same buffer overnight. Precipitates deposited in the dialyzate are removed by centrifugation, and to a supernatant fluid is added ammonium sulfate of 50-70% saturation. Precipitated fractions are thoroughly dialyzed against the same buffer, and passed through a DEAE-cellulose (product of Serva, West Germany) column (5.5×40 cm) equilibrated with 0.01M phosphate buffer (pH 7.0). The column is then washed with 0.01M phosphate buffer (pH 7.0) to remove impure proteins. Thereafter, a concentration gradient of from one l of 0.01M phosphate buffer (pH 7.0) to one l of the same buffer containing 0.2M NaCl is prepared and passed through the column. The active fractions of bilirubin oxidase are eluted and combined. Ammonium sulfate is added to 70% saturation to obtain a precipitate. The precipitate is collected by centrifugation (20,000×g, 20 minutes) and dissolved in 5 ml of 0.01M phosphate buffer (pH 7.0). The solution is passed through a Sephadex G-100 (product of Pharmacia Fine Chemicals, Sweden) column (5.5 ×80 cm) equilibrated with 0.01M phosphate buffer (pH 7.0), and the column is washed with one l of 0.01M phosphate buffer (pH 7.0). The active fractions of the enzyme are combined, and ammonium sulfate is added to 70% saturation. The formed precipitate is recovered by centrifugation (20,000×g, 20 minutes) and dissolved in 10 ml of 0.01M phosphate buffer (pH 7.0). The solution is dialyzed against 5 l of the same buffer for 24 hours. The active fractions are freeze-dried whereby 40 mg of a powdered enzyme preparate, bilirubin oxidase is obtained.

EXAMPLE 2

The same culturing as in Example 1 is carried out except that *Trametes hirsuta* HU8311 is used as a seed strain, and 10.2 l of a culture broth is obtained from 15 l of a culture medium. The enzyme activity of bilirubin oxidase contained in the culture broth is 0.24 unit/ml. The culture broth is subjected to the same purification procedure as in Example 1 to obtain 13 mg of a powdered enzyme preparate.

EXAMPLE 3

The same culturing as in Example 1 is repeated except that the microorganisms identified in Table 1 are used as the seed strain to obtain culture broths containing bilirubin oxidase exhibiting the enzyme activities identified in Table 1.

TABLE 1

| Microorganism | | Enzyme activity (U/ml) |
|---|---|---|
| *Trametes versicolor* | HU8312 | 0.31 |
| *Coriolus consors* | HU8313 | 0.32 |
| *Pholiota nameko* | HU8321 | 0.50 |
| *Pleurotus ostreatus* | HU8331 | 2.20 |
| *Lenzites styracina* | HU8341 | 0.26 |
| *Fomitopsis castanea* | HU8351 | 0.05 |

EXAMPLE 4

An example of prevention against the influence of bilirubin on the determination of free fatty acids 1. Reagents (A) 0.05M phosphate buffer (pH 7.0) containing 40 units/l bilirubin oxidase (B) reagent for the determination of free fatty acids: commercially available Determiner NEFA kit (product of Kyowa Medex Co., Ltd.) which comprises acyl CoA synthetase, acyl CoA oxidase, peroxidase, ATP, CoA methylcarbamoyl-3.7-dimethyl-amino-10H-phenothiazin and good buffer (ph 6.75).

2. Procedure

To 5 test tubes were poured 25 μl of 5 varieties of serum samples free from bilirubin and 0.5 ml of the reagent (A), and the mixture was kept at 37° C. for 10 minutes. Then, 3 ml of the reagent (B) was added thereto, and the mixture was incubated for reaction at 37° C. for 10 minutes according to a conventional manner. The absorption of the reaction solution was measured at 660 nm. In the same manner as mentioned above, the absorption of the same serum samples without a pretreatment with bilirubin oxidase was measured.

Then, to the same serum samples as mentioned above were added 5, 10 or 20 mg/dl bilirubin (product of Sigma) to prepare test samples. Using test samples, the measurement was carried out according to the method of the present invention and the conventional method for comparison.

The results are shown in Table 2 defining a serum sample not containing bilirubin as 100.

TABLE 2

| Sample | Bilirubin concentration (mg/dl) | 0 | 5 | 10 | 20 |
|---|---|---|---|---|---|
| 1 | I | 100 | 94 | 87 | 74 |
|   | II | 100 | 100 | 100 | 99 |
| 2 | I | 100 | 96 | 89 | 83 |
|   | II | 100 | 100 | 100 | 100 |
| 3 | I | 100 | 91 | 84 | 68 |
|   | II | 100 | 10b | 101 | 99 |
| 4 | I | 100 | 98 | 87 | 81 |
|   | II | 100 | 100 | 100 | 100 |
| 5 | I | 100 | 98 | 88 | 78 |
|   | II | 100 | 100 | 99 | 100 |

I: the conventional method
II: the method according to the present invention

While the results on the test samples without pretreatments with bilirubin oxidase considerably undergo the influence of bilirubin in a concentration of 10 mg/dl, those with pretreatments with bilirubin oxidase are prevented from bilirubin in a high concentration of 20 mg/dl. It is concluded that the present invention is useful in avoiding the interference of bilirubin.

We claim:

1. A biologically pure culture of microoganisms selected from the group consisting of *Trametes hirsuta* NRRL 15401, *Trametes versicolor* NRRL 15402, *Coriolus consors* NRRL 15403, *Pholiota nameko* NRRL 15404, *Pleurotus ostreatus* NRRL 15405, *Lenzites styracina* NRRL 15406 and *Fomitopsis castanea* NRR1 15407 which are capable of producing a bilirubin oxidase wherein the bilirubin oxidase is capable of catalyzing a reaction wherein bilirubin is decomposed in the presence of oxygen to form decomposition products which include water but which do not include hydrogen peroxide.

2. A process for producing bilirubin oxidase which comprises the steps of:

culturing a microorganism selected from group consisting of *Trametes hirsuta, Trametes versicolor, Coriolus consors, Pholiota nameko, Pleurotus ostreatus, Lenzites styracins* and *Fomitopsis castanea* which is capable of producing a bilirubin oxidase;
forming the enzyme in the culture broth; and
recovering the enzyme therefrom.

* * * * *

UNITED STATES PATENT AND TRADEMARK OFFICE
CERTIFICATE OF CORRECTION

PATENT NO.  : 4,677,062
DATED       : June 30, 1987
INVENTOR(S) : TAKAYUKI UWAJIMA, ET AL.

It is certified that error appears in the above-identified patent and that said Letters Patent is hereby corrected as shown below:

Column 4, line 28, "1.5% protein" should read
--1.5% soybean protein--.

Column 4, line 33, "30 1-jar containing" should read
--30 1-jar fermenter containing--.

Column 6, line 34, "microoganisms" should read
--microorganisms--.

Column 6, line 39, "NRR1" should read --NRRL--.

Column 6, line 48, "microoganism" should read
--microorganism--.

Column 6, line 48, "from group" should read --from the group--.

Column 6, line 51, "styracins" should read --styracina--.

Signed and Sealed this

Tenth Day of November, 1987

Attest:

DONALD J. QUIGG

*Attesting Officer*      *Commissioner of Patents and Trademarks*